United States Patent
Widerström (10) Patent No.: US 6,698,425 B1
(45) Date of Patent: Mar. 2, 2004

(54) POWDER INHALER (75) Inventor: Carin Widerström, Lund (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/051,518

(22) Filed: Apr. 10, 1998

Related U.S. Application Data (63) Continuation of application No. PCT/SE98/00132, filed on Jan. 29, 1998.

Foreign Application Priority Data

Feb. 7, 1997 (SE) ................................................ 9700424

(51) Int. Cl.$^7$ ........................ A61M 16/00; F16K 11/00; G05D 11/02
(52) U.S. Cl. ............................ 128/203.25; 128/203.15; 128/203.21
(58) Field of Search ....................... 128/203.15, 203.12, 128/203.21, 203.25

(56) References Cited

U.S. PATENT DOCUMENTS

| | | | | |
|---|---|---|---|---|
| 3,967,761 A | * | 7/1976 | Melton, Jr. et al. | 222/194 |
| 4,428,709 A | * | 1/1984 | Peters | 414/412 |
| 4,817,800 A | * | 4/1989 | Williams et al. | 206/484 |
| 5,207,217 A | * | 5/1993 | Cocozza et al. | 128/203.21 |
| 5,349,947 A | * | 9/1994 | Newhouse et al. | 128/203.21 |
| 5,415,162 A | | 5/1995 | Casper et al. | |
| 5,469,843 A | | 11/1995 | Hodson | |
| 5,483,954 A | * | 1/1996 | Mecikalski | 128/203.15 |
| 5,544,646 A | | 8/1996 | Lloyd et al. | |
| 5,568,807 A | * | 10/1996 | Mecikalski | 128/203.21 |
| 5,575,281 A | * | 11/1996 | Mecikalski | 128/203.21 |
| 5,590,645 A | * | 1/1997 | Davies et al. | 128/203.15 |
| 5,694,920 A | * | 12/1997 | Abrams et al. | 128/200.16 |
| 5,785,049 A | * | 7/1998 | Smith et al. | 128/203.15 |
| 5,860,419 A | * | 1/1999 | Davies et al. | 128/203.15 |
| 5,873,360 A | * | 2/1999 | Davies et al. | 128/203.15 |
| 5,881,719 A | * | 3/1999 | Gottenauer et al. | 128/203.15 |
| 6,089,228 A | * | 7/2000 | Smith et al. | 128/203.15 |

FOREIGN PATENT DOCUMENTS

| | | | | |
|---|---|---|---|---|
| DE | 4400084 | | 7/1995 | |
| DE | 19523516 | | 10/1996 | |
| EP | 0237507 | | 12/1991 | |
| EP | 0469814 | | 2/1992 | |
| WO | 94/12230 | | 6/1994 | |
| WO | 97/02061 | | 1/1997 | |
| WO | WO 98/34664 | * | 8/1998 | 128/203.15 |

OTHER PUBLICATIONS

International Search Report.

* cited by examiner

Primary Examiner—Aaron J. Lewis
Assistant Examiner—Joseph Weiss
(74) Attorney, Agent, or Firm—Fish & Richardson P.C.

(57) ABSTRACT

A dry powder inhaler for use with a blister pack is disclosed. The inhaler has a dosing mechanism that releases powder from a variable number of blisters in the blister pack into an inhalation channel, such that the actual dose administered by the inhaler can be varied with each use of the inhaler.

7 Claims, 6 Drawing Sheets

POWDER INHALER

This is a continuation of International Patent Application No. PCT/SE98/00132, with an international filing date of Jan. 29, 1998, now pending.

BACKGROUND

The present invention relates to a powder inhaler, a blister pack and a method of dispensing powder. More particularly, it relates to a means and method by which a patient may inhale a variable dose of medicament.

It is known that powder containing a medicament may be inhaled for the treatment of certain conditions, such as asthma. Various systems have been proposed for storing and administering the powder.

U.S. Pat. No. 5,469,843 discloses a system in which a tape is coated with the powder and a sprung hammer strikes the back of the tape to release the powder. WO 94/12230 discloses a device in which an elongate blister pack is successively advanced through the device and in which means are provided for opening a blister and releasing a dose of powder. EP-A-0237507 discloses a device having a bulk powder reservoir from which doses of powder are successively transferred into an inhalation channel.

These various systems all have their own particular advantages and disadvantages, but these will not be considered here.

A disadvantage in common with all of these previous systems is that, within each type of system, it is necessary to provide a wide selection of different inhalers catering for users with different needs and for medicaments requiring different doses.

According to the present invention, there is provided a dry powder inhaler for use with a blister pack having a plurality of blisters, each blister containing a predetermined quantity of powder, the inhaler comprising:

an inhalation path; and dosing means for opening the blisters and releasing the powder into the inhalation path for inhalation by the user, wherein the dosing means comprises opening means suitable for simultaneously opening a predetermined plurality of said blisters such that, for each use of the inhaler, the actual dose administered is determined by the number of previously unopened blisters which are opened by the opening means.

The dosing means may comprise a control means for controlling the opening means to open a desired number of the blisters. Alternatively, for each use of the inhaler, the opening means may operate to open all of the predetermined plurality of blisters, the blister pack being positioned in the dosing means according to the required dose, such that the actual dose administered is determined by the number of unopened blisters on which the opening means operates.

In conjunction with this inhaler, the present invention also provides a blister pack comprising a plurality of blisters, each containing a predetermined quantity of powder for inhalation wherein each blister contains less than the clinical effective dose of said powder according to the particular one or more substances contained in the powder.

Thus, according to the present invention there is also provided a method of dispensing powder from a blister pack having a plurality of blisters, each blister containing a predetermined quantity of powder, the method comprising:

opening blisters of the blister pack so as to release the powder contained in said blisters into a delivery channel; and choosing the number of blisters to be opened so as to provide the powder from said number of blisters in the delivery channel at the same time, the number being determined according to the quantity of powder required to be released into the delivery channel.

The present invention gives rise to many advantages.

Previously, for any one particular medicament, it was necessary to produce a selection of blister packs having respective blisters containing different doses. For instance, one blister pack would be produced having blisters containing the powder dose for an adult and another blister pack would be produced having blisters containing the powder dose for children. Clearly, the need to produce different types of blister pack adds to their cost of production. The present invention allows a single type of blister pack to be used for users with different needs. For instance, for the example given above, a child could use a dose of three blisters whereas an adult could use a dose of five blisters.

Similarly, while previous inhalers require a user to inhale two or more separate doses to receive an extra large dose, the present invention allows the dosage to be varied with a single inhalation.

Another advantage is that only one design of inhaler need be constructed to cater for a variety of blister packs respectively containing many different types of medicament. Any variations required in the dosing between the various different types of medicament may be easily accomplished by the inhaler, which will merely open the required number of blisters.

The present invention allows additional flexibility which has not before been contemplated. In particular, the size of a dose can be varied for each inhalation. This is important for some patients, since their need of medicament can vary, for instance according to the time of day, their body activity or their food intake. In this respect, the present invention is particularly useful in conjunction with antidiabetic substances, such as insulin.

Indeed, according to the present invention, there is also provided a blister pack comprising a plurality of blisters, each containing a predetermined quantity of medicament for inhalation wherein the medicament comprises an antidiabetic medicament.

Medicaments suitable for use with the present invention are any which may be delivered by inhalation. Suitable inhalable medicaments may include for example β2-adrenoreceptor agonists for example salbutamol, terbutaline, rimiterol, fenoterol, reproterol, adrenaline, dpirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators for example ipratropium bromide and the like; glucocorticosteroids for example beclomethasone, fluticasone, budesonide, tipredane, dexamethasone, betamethasone, fluocinolone, triamcinolone acetonide, mometasone, and the like, and their pharmacologically acceptable esters and salts; anti-allergic medicaments for example sodium cromoglycate and nedocromil sodium; expectorants; mucolytics; antihistamines; cyclooxygenase inhibitors; leukotriene synthesis inhibitors; leukotriene antagonists, phospholipase-A2 (PLA2) inhibitors, platelet aggregating factor (PAF) antagonists and prophylactics of asthma; antiarrhythmic medicaments, tranquilisers, cardiac glycosides, hormones, antihypertensive medicaments, antidiabetic-, such as insulin, antiparasitic- and anticancer-medicarnents, sedatives and analgesic medicaments, antibiotics, antirheumatic medicaments, immunotherapies, antifungal and antihypotension medicaments, vaccines, antiviral medicaments, proteins, polypeptides and peptides for example peptide hormones and growth factors, polypeptides vaccines, enzymes, endorphines, lipoproteins and polypeptides involved in the blood coagulation cascade, vitamins and others, for example cell surface receptor blockers, antioxidants, free radical scavengers and organic salts of N,N'-diacetylcystine.

The present invention will be more clearly understood from the following description, given by way of example only, with reference to the accompanying drawings.

DESCRIPTION OF THE PREFERRED EMBODIMENTS

Inhalers according to the present invention are preferably to be used with any blister pack containing suitable powder, where each blister contains less than a clinical effective dose of the powder according to the particular medicament contained in the powder such that two or more blisters must be opened to obtain a full dose. However, such inhalers can also be used with blister packs having a clinical effective dose in each blister. Of course, the inhalers would not then be able to administer less than that dose.

Figure 1A:
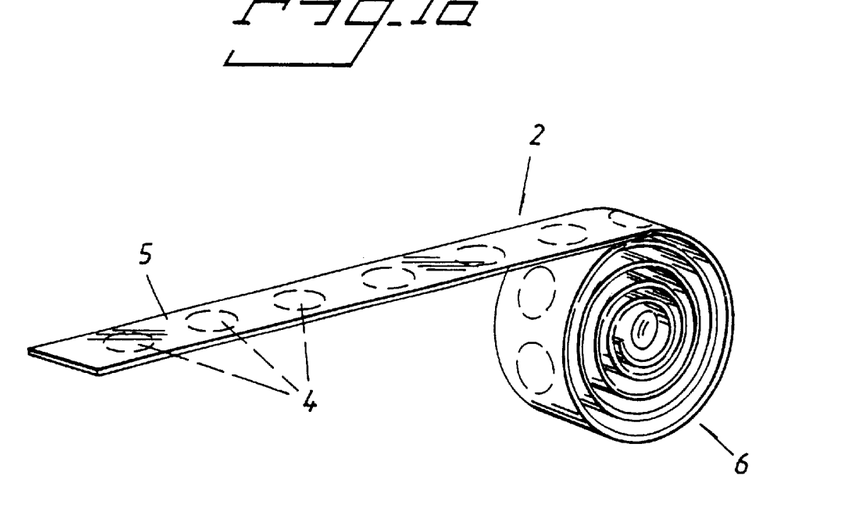
FIGS. 1(a) and 1(b) illustrate a blister pack according to the present invention.
Figure 1B:
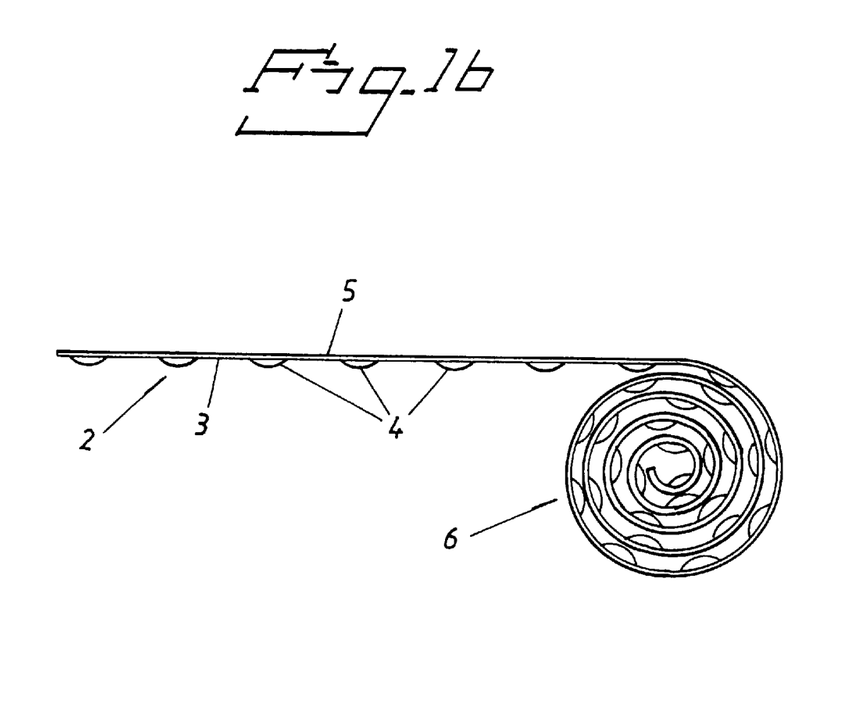

FIGS. 1(a) and 1(b) illustrate a blister pack 2 which is provided as a roll 6. The blister pack is formed from a continuous layer 3 with a series of cavities 4 along its length. Each cavity 4 is filled with a suitable powder and then sealed by a sealing layer 5 which covers the surface of the continuous layer 3. Preferably, perforations exist between each blister, allowing used blisters to be torn off.

Figure 2A:
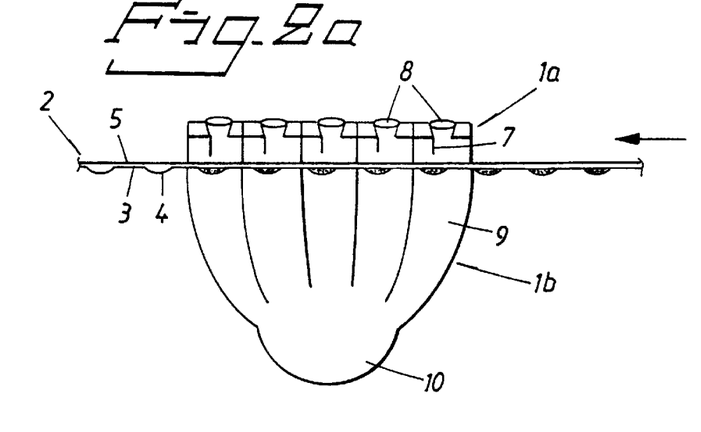
FIGS. 2(a), 2(b) and 2(c) illustrate schematically the operation of a first embodiment of the present invention.
Figure 2B:
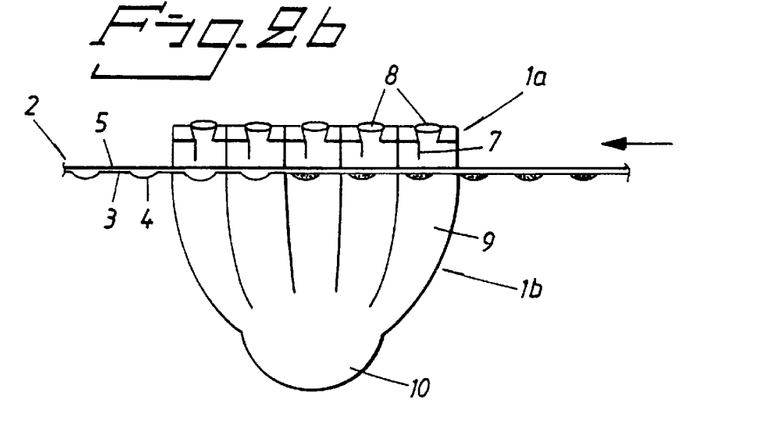
Figure 2C:
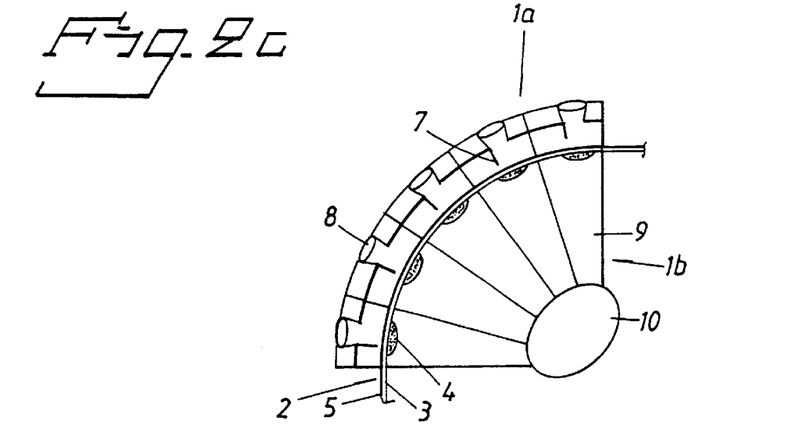

The blister pack 2 is inserted into an inhaler 1 as illustrated schematically in FIGS. 2(a), 2(b) and 2(c).

The inhaler 1 has a first part 1a which functions to open the blisters and a second part 1b which guides air and the powder released from the blisters out of a mouthpiece of the inhaler.

Part 1a of the inhaler 1 is provided with a plurality of cutting means 7 and associated air inlets 8. The cutting means 7 may comprise any suitable means for rupturing the sealing layer 5 of the blister pack 2 and, in some embodiments such as those of FIG. 2, for rupturing the lower cavity 4 wall also. In particular, curved or straight blades or pin like members may be used.

In use, with the blister pack 2 inserted in the inhaler 1, the part 1a of the inhaler 1 is moved towards the blister pack such that each of the cutting means 7 ruptures a corresponding blister 4. As illustrated in FIGS. 2(a), (b) and (c), the cutting means perforate not only the sealing layer 5, but also the continuous layer 3 where it forms the cavities 4. In this way, powder contained in the blisters 4 is released into part 1b of the inhaler 1 below or, at least, is sucked through into part 1b during inhalation by the user.

Part 1b of the inhaler 1 has a series of channels 9 corresponding to the cutting means 7 and air inlets 8 of part 1a. The channels 9 extend to a common inhalation channel 10. Thus, after part 1a of the inhaler 1 has been moved so as to rupture the blisters 4, a user may inhale through the inhaler 1 such that air is drawn through the air inlets 8, picks up powder from the ruptured blisters 4 and passes out of the inhaler via the channels 9 and common inhalation channel 10.

As will be seen by reference to FIG. 2(b), if the blister pack 2 is only partly advanced under the cutting means 7 of part 1a of the inhaler 1, when the inhaler 1 is operated, some of the cutting means 7 operate on blisters 4 which have already been ruptured and emptied. In this way, the quantity of powder administered in a single use of the inhaler can be varied.

As mentioned before, the illustrations of FIGS. 2(a) and (b) are merely schematic and a number of variations are possible.

Firstly, the cutting means 7 need not be provided with individual respective inlets 8, but could be fed with air from a common inlet.

Secondly, the inhaler need not be provided with separate channels 9 and powder from the blisters 4 could move directly into a common inhalation channel.

Thirdly, as illustrated in FIG. 2(c), the path of the blister pack 2 need not be straight, but could proceed along a curve.

Figure 3A:
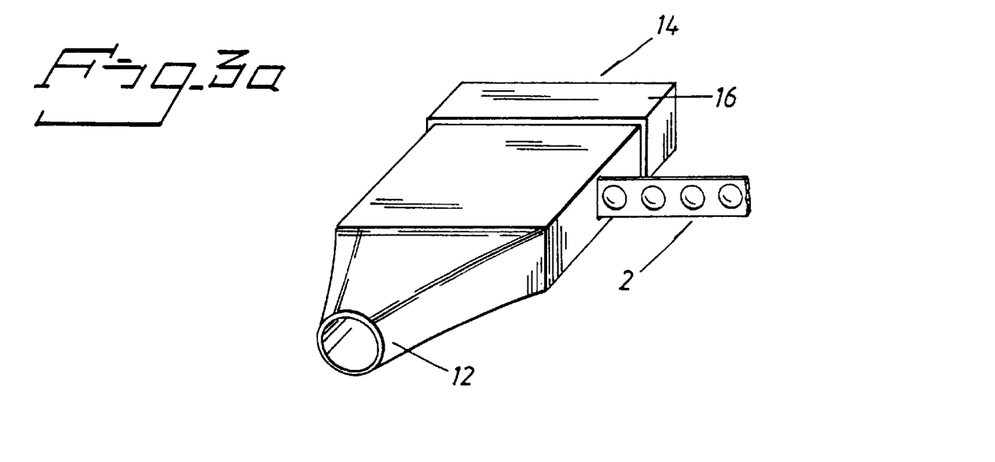
FIGS. 3(a) and (b) illustrate an inhaler embodying the present invention.

FIGS. 3(a) and (b) illustrate the basic features of an inhaler such as described above, FIGS. 3(b) showing a cross-section of the device of FIG. 3(a).

Figure 3B:
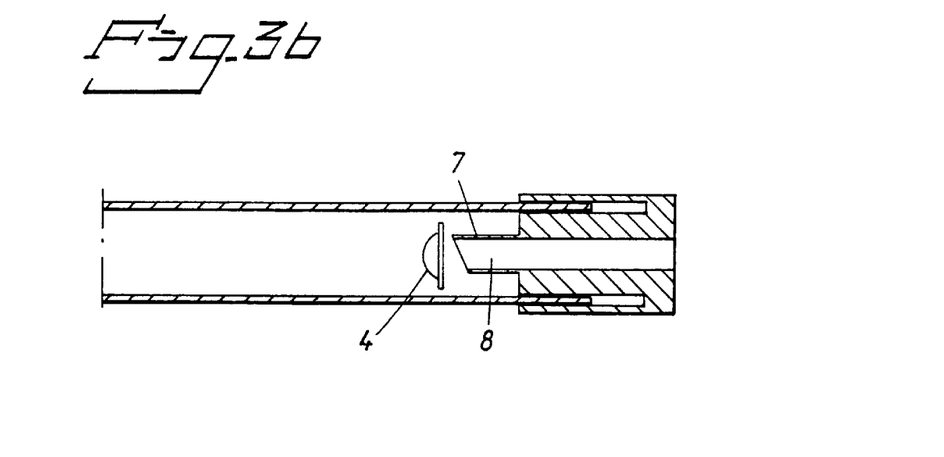

The inhaler 1 has a mouthpiece 12, an inlet opening 14 and an opening means 16. The opening means 16 is axially moveable on one end of the inhaler, preferably against the resistance of a spring which is not shown. It includes a plurality of cutting means 7 each for use with a corresponding blister 4. It also includes a plurality of air inlets 8 corresponding to the cutting means 7. The inlet opening 14 may be formed as a plurality of openings, each forming an end of an air inlets 8 or alternatively as a single opening which feeds the air inlets 8.

In use, once the blister pack 2 has been inserted by an appropriate amount the opening 15 means 16 is pushed towards the mouthpiece 12 such that each cutting means 7 cuts through its corresponding blister 4. With the opening means 16 released, the user may then inhale through the mouthpiece 12, drawing air from the air inlets 8 through the blisters 4 so as to pick up powder in the air stream.

Figure 4A:
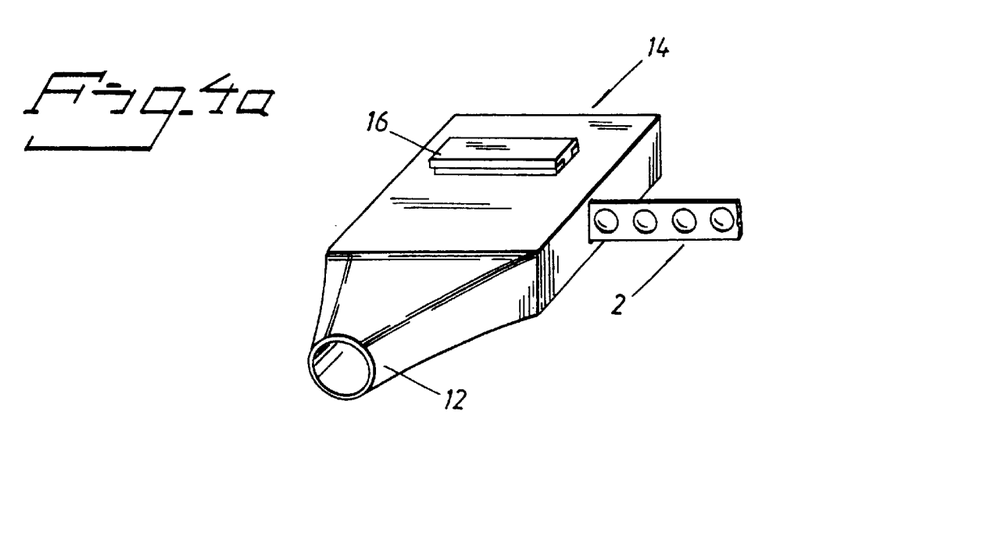
FIGS. 4(a) and (b) illustrate an inhaler embodying the present invention.
Figure 4B:
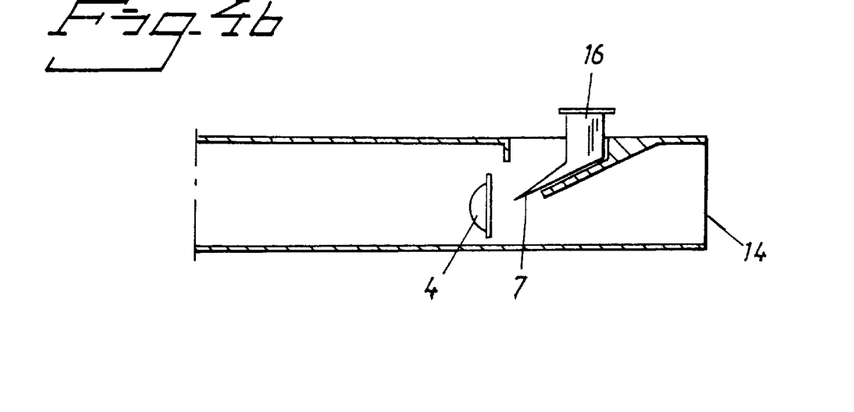

FIGS. 4(a) and (b) illustrate a similar device in which the opening means 16 takes the form of a button on a side face of the inhaler.

As may be seen from the cross-section shown in FIG. 4(b), when the button 16 is depressed, the cutting means 7 are directed through the corresponding blisters 4 so as to perforate them. FIG. 4(b) is only schematic and a number of preferred features are not illustrated. For instance, it is preferable to seal the button 16 arrangement such that air only enters the inhaler via inlet opening 14. It is also preferable to provide a spring to return the button 16 and cutting means 7 to their original positions.

Another inhaler according to the present invention will now be described with reference to FIGS. 5(a) and 5(b).

As with the embodiments described above, the inhaler 1 has a mouthpiece 12, an inlet opening 14 and an opening means 16. In use, a blister pack 2 is inserted into the inhaler 1 according to the number of blisters 4 to be used and the opening means 16 is pressed down into the inhaler 1 so as to rupture those blisters. By inhaling through the mouthpiece 12, air is drawn in through inlet 14, picks up powder from the ruptured blisters 4 and is inhaled.

Figure 5A:
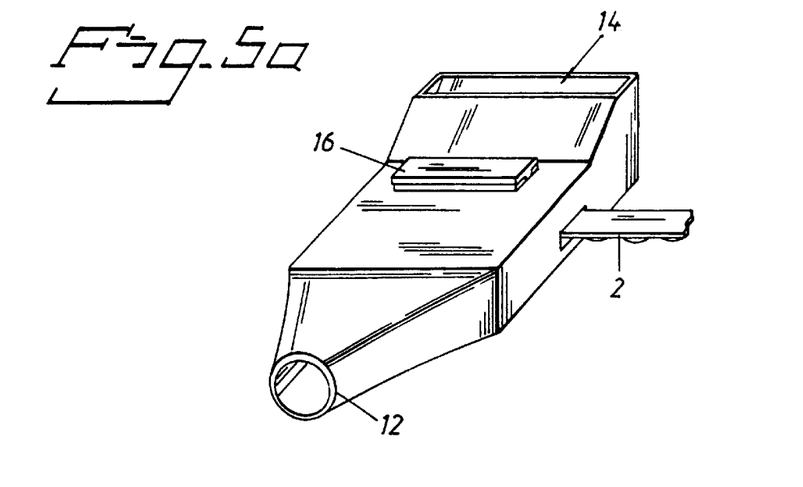
FIGS. 5(a) and (b) illustrate an inhaler embodying the present invention.

The embodiment of FIGS. 5(a) and (b) differs from those described above by virtue of the fact that the cutting means 7 only rupture the sealing layer 5 and the air stream is ducted down onto and over the ruptured blisters.

Figure 5B:
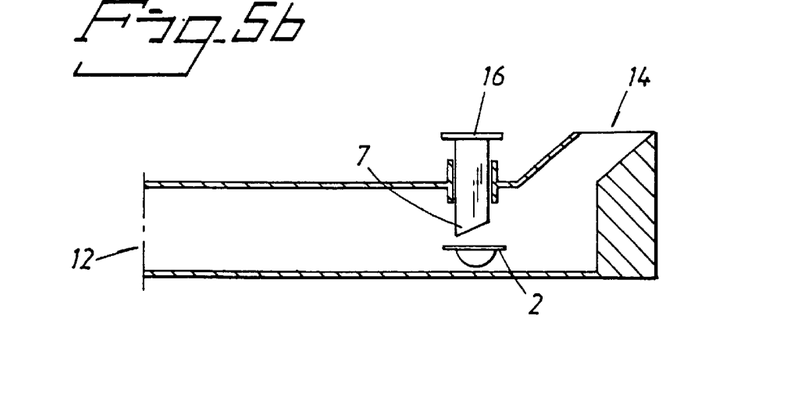
Figure 6:
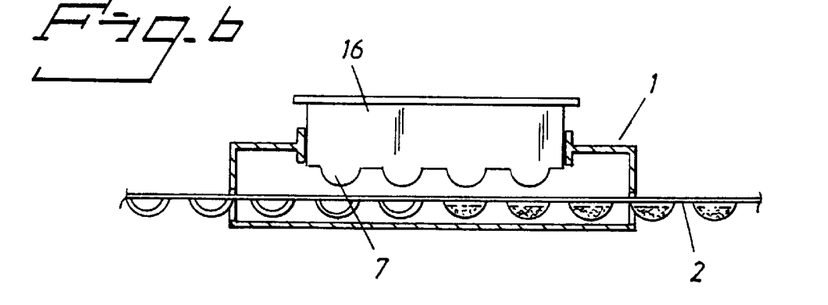
FIG. 6 illustrates a cross-section of an inhaler according to a first embodiment of the present invention.

FIG. 6 illustrates a cross-section of the embodiment of FIG. 5(b) and shows how the opening means 16 can operate to open a plurality of blisters simultaneously, even those which have already been opened. An equivalent arrangement can easily be derived for the embodiment of FIG. 4(b).

The operation described so far can be considered as a first embodiment of the present invention. A second embodiment will now be described.

In the second embodiment, rather than the first part 1a of the inhaler 1 operating as a single unit, it is possible for each of the cutting means 7 (possibly together with their corresponding air inlets 8) to be operated independently. In this way, even when the blister pack 2 is advanced entirely under part 1a of the inhaler 1 as illustrated in FIG. 2(a), it is still possible to rupture only some of the blisters 4 which are positioned adjacent the cutting means 7.

Preferably, the blisters 4 which are ruptured are those furthest downstream of the blister pack, such that, after a use, the blister pack may be advanced by the number of blisters 4 which were ruptured during that use so as to once again arrive at the arrangement illustrated in FIG. 2(a). Preferably, the inhaler 1 is also provided with a mechanism which, after a number of blisters 4 are ruptured, only allows the blister pack 2 to be advanced by that number of blisters 4.

Figure 7:
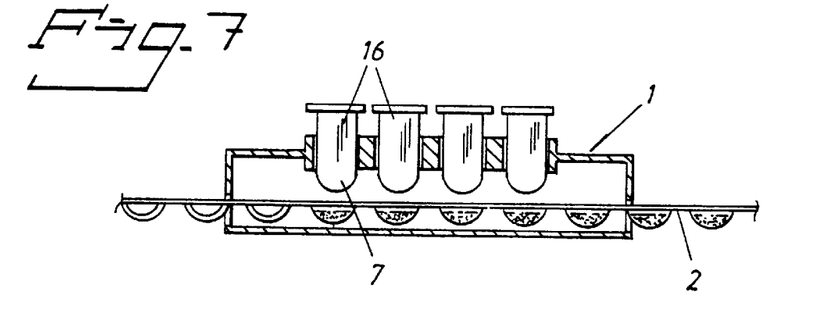
FIG. 7 illustrates a cross-section of an inhaler according to a second embodiment of the present invention.

FIG. 7 illustrates a variation of the inhaler of FIG. 5(b) which relates to the second embodiment As may be seen, the opening means 16 of FIG. 6 is replaced by a plurality of opening means 16. The opening means 16 thus comprises a means for controlling the number of blisters to be opened. In particular, the number of blisters which are opened is determined by the number of opening means 16 which are depressed by the user. An equivalent arrangement may easily be derived for the embodiments of FIGS. 3(a) and 4(a).

Figure 8:
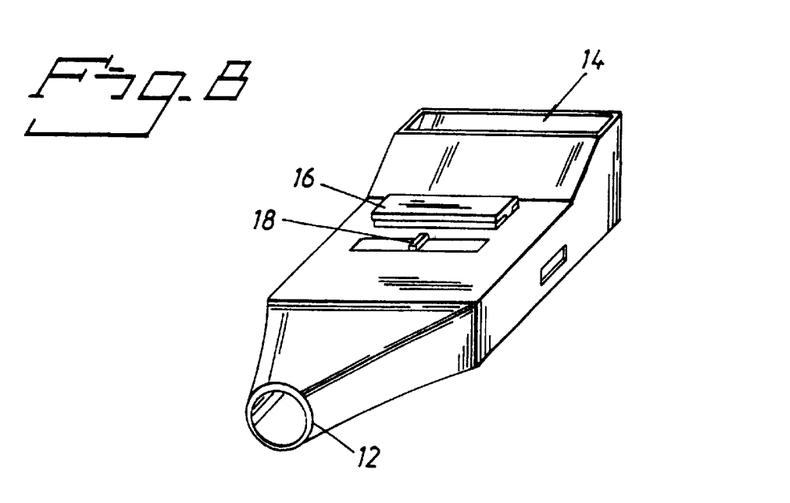
FIG. 8 illustrates a variation of the inhaler of FIG. 7.

FIG. 8 illustrates a more sophisticated variation of the inhaler of FIG. 7 in which a single opening means 16 is provided.

The inhaler of FIG. 8 comprises an additional control means 18 with a slider which indicates the selected dosage and a control mechanism controlled by the slider. By altering the position of the slider, the control mechanism varies the number of the cutting means 7 which are engaged by the opening means 16. In this way, the user only operates one opening means 16, but ruptures the number of blisters 4 required for the particular dose.

The control mechanism may also include a moveable stop or a ratchet mechanism, such that the blister pack 2 can only be inserted to a particular position or advanced by a certain number of positions.

Clearly, a slider 18 can also be incorporated in the embodiments of FIGS. 3(a), 4(a) and 5(a) so as to control the stop position or advancement amount of the blister pack 2.

The slider can of course be replaced by any other control, such as a rotatable knob.

The devices described so far have only been described with reference to a blister pack 2 which is manually inserted/ advanced. However, preferably, when the blister pack 2 is provided as a roll 6 such as illustrated in FIGS. 1(a) and (b), it is installed into the inhaler as a roll and automatically unwound and advanced through the inhaler. The used length of the blister pack 2 can then either exit the inhaler or be wound inside another portion of the inhaler. In the case of first embodiments such as described with reference to FIGS. 3 to 6, the blister pack 2 should be advanced under the cutting means so as to provide only as many unopened blisters 4 under the cutting means 7 as required. According to this embodiment, the blister pack 2 may be advanced immediately after the inhaler is used or immediately before its next use. It is advantageous for the blister pack 2 to be advanced immediately before each use, because the number of used blisters which are advanced out of the inhaler corresponds to and gives a visual indication of how many blisters are about to be used. Indeed, if the user leaves those used blisters in place, upon using the inhaler again, there is an indication of how many blisters were used previously. This is particularly advantageous when the user has to take different doses alternately. For instance, to obtain an average dose corresponding to 3½ blisters, a user can alternately use 3 and 4 blisters.

In the case of second embodiments such as described with reference to FIG. 7, the blister pack 2 should be advanced by the number of blisters 4 previously used. This can easily be achieved by a mechanical ratchet arrangement, with the dosage being set by the user. Alternatively, a more complex electronic arrangement might be provided with motorised advance of the blister pack and detectors to determine which blisters 4 have been already used.

Where the blister pack is advanced out of the inhaler 1, a cutter, such as a blade may be provided at the exit to facilitate used blisters being removed.

Where a blister pack 2 is to be manually inserted, it may be provided as a straight elongate pack. For first embodiments, the blister pack would be inserted merely as far as necessary, whereas, for second embodiments, it would be fully inserted. According to this arrangement, it is possible to provide an inhaler having only an inlet portion whereby, after each use, the user tears off unused blisters from the end of the blister pack, for instance by use of the previously mentioned perforations. For embodiments of the first type, a moveable stop may then be provided to ensure that the blister pack is not inserted further than necessary.

It should be noted that inhalers embodying the present invention are not limited to use with elongate blister packs as illustrated in FIGS. 1(a) and (b). Any other layout of blisters may also be used.

Figure 9A:
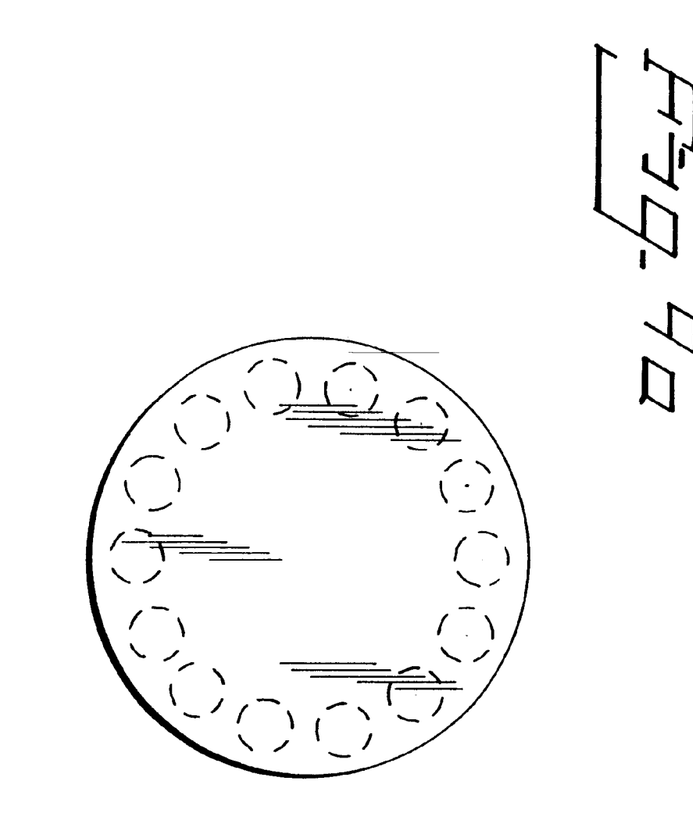
FIGS. 9(a) and 9(b) illustrate alternative blister packs.

FIG. 9(a) illustrates a blister pack in which blisters are arranged circularly on a disk. With this blister pack, the amount by which the disk is rotated between uses will vary according to the number of blisters ruptured.

Figure 9B:
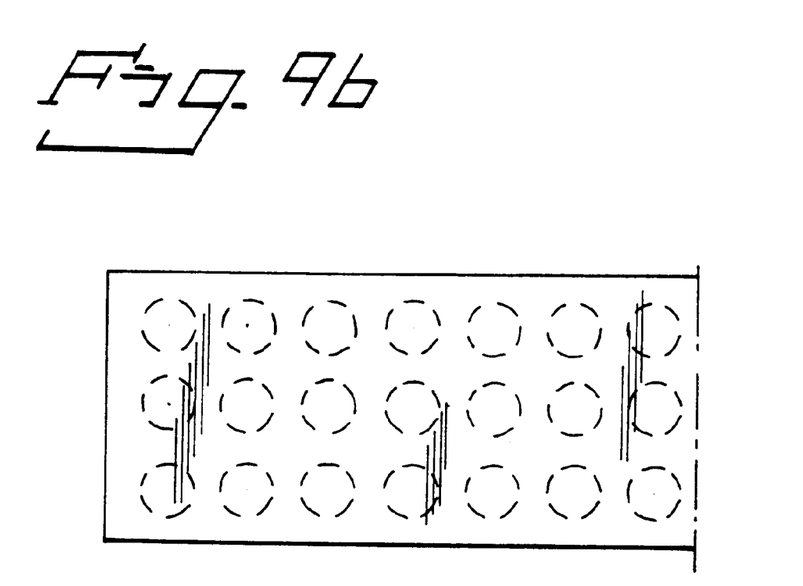

FIG. 9(b) illustrates a blister pack with blisters arranged across the width of the blister pack as well as along its length. With this blister pack, it is possible that the blister pack is advanced by one row of blisters upon each use, with the dosage administered being controlled according to the number of blisters ruptured across the width of the blister pack.

It is also possible to construct a device which simultaneously accepts two or more blister packs respectively containing different amounts of medicament. In its most straight forward form, the device receives two or more blister pack strips of the type illustrated in FIG. 1 and guides them to two parallel sets of cutting means 7 as illustrated in FIGS. 6 and 7. The user can then individually advance each respective blister pack strip according to the dose required. In particular, when one blister pack strip includes smaller amounts of the medicament than the other strip(s) greater variability may be provided for the administered dose. One blister pack will provide coarse variability and the other blister pack fine variability. Preferably, the device includes a mechanism such that a single operation of the user ruptures blisters of all the strips.

Finally, some consideration should be given to the amount of powder stored in each blister of a blister pack embodying the present invention.

In practice, blister packs are produced having blisters which each contain a clinical effective dose of a particular medicament for any application.

The following medicaments could be administered with the following ranges:

| Compound | Dose range |
|---|---|
| Budesonide | 50 µg–1600 µg |
| Terbutaline | 125 µg–12 µg |
| Formoterol | 3 µg–48 µg |
| Salbutamol | 50 µg–6–700 µg |
| Salmeterol | 50 µg–200 µg |
| Fluticason | 50 mg–1000 mg |

The quantity of medicament stored in each blister should therefore be appropriate to provide a reasonable cover over at least central portions of these ranges according to the maximum number of blisters to be opened simultaneously, for instance between 2 and 8.

In general, it is proposed that each blister should contain one of 10–75%, 20–50%, ¼, ⅓ and ½ of the clinical effective dose. It is particularly advantageous to provide fractions of the clinical effective dose, since this makes it easier for a patient to determine how many blisters to dispense.

For medicaments, such as antidiabetic medicaments, where the requirements of a user vary continuously between small doses and relatively large doses, the present invention is ideal. With an antidiabetic medicament contained in blisters, the dose of that medicament may be varied according to the needs of the patient.

For instance, for insulin, the required dose might vary between 0.1 mg (1 unit) and 2.0 mg (20 units). Preferably, therefore blisters can be provided containing a suitable quantity of insulin to cover this range or at least a more normal range within it. In this regard, it is proposed to use blisters containing one of 0.05–0.15 mg, 0.15–0.25 mg, 0.25–0.35 mg and 0.35–0.45 mg (½–1½ units, 1½–2½ units, 2½–3½ units, 3½–4½ units). In particular, blisters containing 2 units each would allow a range of 2 to 8 units with only 4 blisters per use.

What is claimed is:

1. A dry powder inhaler for use with a blister pack having a plurality of blisters, the blisters containing predetermined quantities of powder, the inhaler comprising:

an inhalation path, walls defining a chamber, the chamber being sized and shaped to receive a portion of the blister pack while another portion of said blister pack is outside of said chamber, and the chamber being in communication with the inhalation path;

an advancement mechanism that advances the blister pack through the chamber so as to place said another portion of said blister pack within the chamber and a portion of said blister pack that had been in said chamber outside of said chamber; and a dosing mechanism that provides a variable dose of powder from the blister pack to the inhalation chamber, the dosing mechanism including an opener configured to simultaneously open blisters disposed within the chamber, such that, for each use of the inhaler, the variable dose of powder administered is determined by the number of previously unopened blisters opened by the opener;

wherein the dosing mechanism further comprises a controller that allows a user to select a desired number of blisters to be opened by the opener, further comprising;

a stop member that restricts advancement of the blister pack to an extent corresponding to a number of blisters opened during a previous use of the inhaler.

2. The inhaler of claim 1, wherein the stop member is selected from the group consisting of a movable stop, a slider, and a ratchet mechanism.

3. The inhaler of claim 1, wherein the opener is at least partly disposed within the chamber.

4. The inhaler of claim 1, wherein the opener comprises a cutting blade.

5. The inhaler of claim 4, wherein the opener comprises a plurality of cutting blades, each blade arranged to open a separate blister.

6. The inhaler of claim 1, further comprising a section adapted to store an unused portion of the blister pack.

7. The inhaler of claim 1, wherein the dosing mechanism is configured to release powder from an elongated blister pack having blisters arranged along its length.

* * * * *